United States Patent [19]

Scavuzzo et al.

[11] Patent Number: 5,507,194
[45] Date of Patent: Apr. 16, 1996

[54] DISPOSABLE BAILER

[75] Inventors: William Scavuzzo, Clark; Wilton Hawkins, Montclair, both of N.J.

[73] Assignee: Norton Performance Plastics Corporation, Worcester, Mass.

[21] Appl. No.: 361,027

[22] Filed: Dec. 21, 1994

Related U.S. Application Data

[63] Continuation of Ser. No. 132,400, Oct. 6, 1993, abandoned.

[51] Int. Cl.[6] ............................................. G01N 1/12
[52] U.S. Cl. ............................................. 73/864.63
[58] Field of Search ........................... 73/864.63–864.67

[56] References Cited

U.S. PATENT DOCUMENTS

| | | | |
|---|---|---|---|
| 1,621,857 | 3/1927 | Seraphin | 73/864.65 |
| 4,050,315 | 9/1979 | Markfelt | 73/864.66 |
| 4,271,704 | 6/1981 | Peters | 73/864.63 |
| 4,590,810 | 5/1986 | Hunkin et al. | 73/864.63 |
| 4,846,004 | 7/1989 | Richards et al. | 73/864.63 |
| 4,949,582 | 8/1990 | Vollweiler | 73/864.63 |
| 5,139,654 | 8/1992 | Carpenter | 73/864.63 |
| 5,219,364 | 6/1993 | Lloyd . | |

FOREIGN PATENT DOCUMENTS 0838500  6/1981  U.S.S.R. ............................ 73/864.67

*Primary Examiner*—Robert Raevis
*Attorney, Agent, or Firm*—Stephen L. Borst; Mary E. Porter

[57] ABSTRACT

The present invention is a disposable bailer having an elongated tube with opposite inlet and outlet ends of the tube, both ends being integral with the tube and tapered; with an inlet valve means, the inlet end of the tube being continuously molded with the tube to form an internal cavity for containing the inlet valve means.

7 Claims, 1 Drawing Sheet

DISPOSABLE BAILER

"This is a continuation of application Ser. No. 0 8/132, 400 filed on Oct. 6, 1993 (now abandoned).

BACKGROUND OF THE INVENTION

1. Field of the Invention

The invention relates to an inexpensive disposable bailer for use in environmental sampling.

2. Technology Review

Environmental sampling devices, in many instances, must be of a prescribed level of cleanliness before use. The more expensive types of samplers, for economic reasons, must be reused. This, therefore, requires the device to be disassembled, cleaned, and reassembled before each use. This can result in substantial cleaning costs to the sampling contractor.

Certain liquid sampling devices or bailers in the market may be considered "disposable" however these bailers are generally more expensive to manufacture because of their multi-component construction and because of the quantity of materials required in the construction of the bailer. The parts of these bailers are either threaded or welded together which creates a possible source for residual contaminates and leakage, and certainly increases the manufacturing costs.

These bailers further utilize a "free floating" ball which when seated in the inlet (bottom) end of the tubular device functions as a plug or stopper to prevent fluid from escaping through the inlet opening. While these bailers satisfactorily contain the contents of the bailers as long as they are held in a vertical position, a problem can occur when tilting and pouring from the top of these bailers, in that the ball can dislodge from its seat resulting in spillage from the inlet opening. These types of bailers are, therefore, more difficult to control when releasing the sample.

The objective of this invention is to provide a single-use disposable bailer which is inexpensive to manufacture. A further objective of this invention is to provide a single-use disposable bailer which is structurally designed to require less material in its construction and to descend or ascend when sampling without snagging on obstructions. A further objective of this invention is to provide for a single-use disposable bailer which has a inlet valve means with a more secure and improved flow control. A further objective is to provide a single-use disposable bailer with a one-piece bailer body construction eliminating the need for threaded or welded body components.

SUMMARY OF THE INVENTION

The present invention is a disposable bailer comprising an elongated tube with opposite (upper and lower) ends tapered and the lower end containing an inlet valve means. Both ends of the bailer are continuously molded with the tubular body, the lower end being molded to form an internal cavity for containing the inlet valve means.

DETAILED DESCRIPTION OF THE INVENTION

Figure 1:
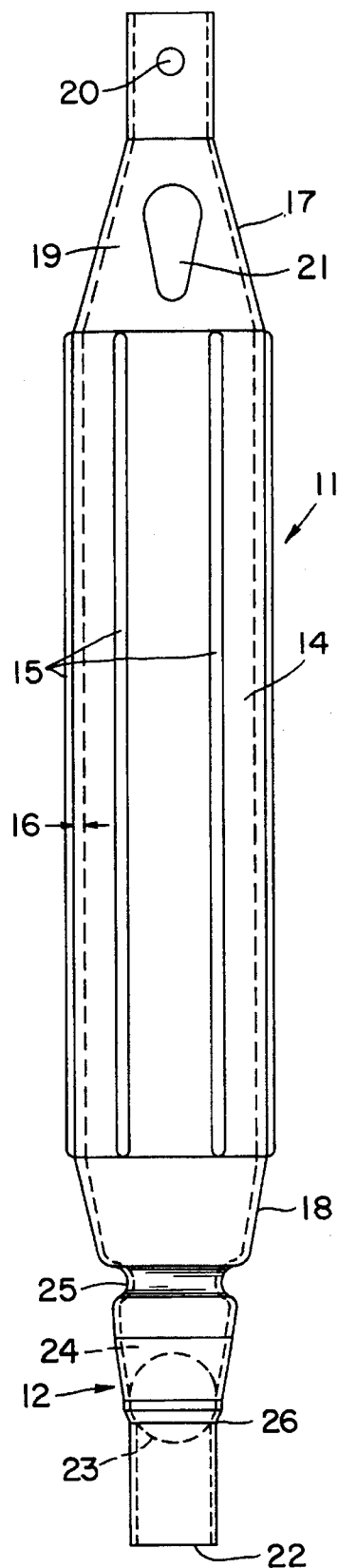
FIG. 1 is a frontal view of the disposable bailer of the invention.

The bailer 11, see FIG. 1, of this invention requires only two components: the bailer body 14 itself, and an inlet valve means 12. The bailer body 14 is of one-piece construction, eliminating the need for threaded or welded body components which could be a possible location for leakage or for trapping contaminates. This also lowers manufacturing costs. While a circular shaped cross section is preferred for the tubular design of the bailer body, the bailer may have a square or multi-sided shaped cross-section.

The ends of the bailer body may feature a tapered design 17, 18 which act to prevent the bailer, during descent or ascent, from becoming snagged on any obstructions which might exist within the area being tested. The tapered upper end 19 of the bailer may also contain a means for suspending the bailer such as at least one suspension cord hole 20 and/or another emptying means besides the inlet valve means such as a pour spout 21 for releasing an obtained sample.

The bailer body 14 can have various structural modifications such as molded-in ribs 15 which act as stiffening agents to allow for minimal wall thickness (economize material use) while still achieving the needed rigidity to prevent the bailer body from collapsing or folding when the unit is full of liquid.

The wall thickness 16 of the bailer can vary throughout the body 14 and its tapered ends. For example, the wall at the upper end of the bailer can be thickened to give additional strength at the point where the bailer and its contents are supported by the suspension cord. Thus, the wall thickness through out the body may vary from as little as 0.13 mm to as much as 2.0 mm.

While the bailer can be constructed of many different materials, i.e. metals, glass, or polymers such as for example polyvinyl chloride, polyethylene, or polytetrafluoroethylene. Polymers are the preferred material and the chemical inertness and economics required make FEP fluoropolymer (fluorinated ethylene propylene) and polypropylene the more preferred materials. Both of these polymers further provide the desired optical properties with the FEP fluoropolymer being transparent and the polypropylene being translucent. These features permit the user to easily determine the sample level and to view boundary layers of any immiscible liquids. If polypropylene is used for the bailer body 14 a weight 30 has to be incorporated into the bailer body because of the specific gravity of polypropylene to offset its buoyancy and permit the bailer 11 to sink rapidly in a well or any other area being tested. Preferably this weight is located near the bottom of the bailer, allowing it to descend in an upright position and fill properly in open bodies of water such as lakes, ponds, reservoirs, or streams. After use, the ring may be easily removed for recycling purposes by crushing the bailer body.

The inlet valve means 12 may consist of for example a ball 23 or any other shaped object which functions as a valve and which rests in a seat 26 formed in the body 14. To constrain the longitudinal motion of the ball when emptying through the pour spout 21 the configuration of the body 14 at the location just above the ball 23 is constricted to a dimension slightly smaller than the diameter of the ball 23. This can be done with appropriate indentations 25 which narrow or neck in the taper at that point. During assembly the ball 23 is easily placed in its location by pushing it through the restriction 25. The resilience of the body 14 allows the ball to be thus installed with minimum force.

Figure 2:
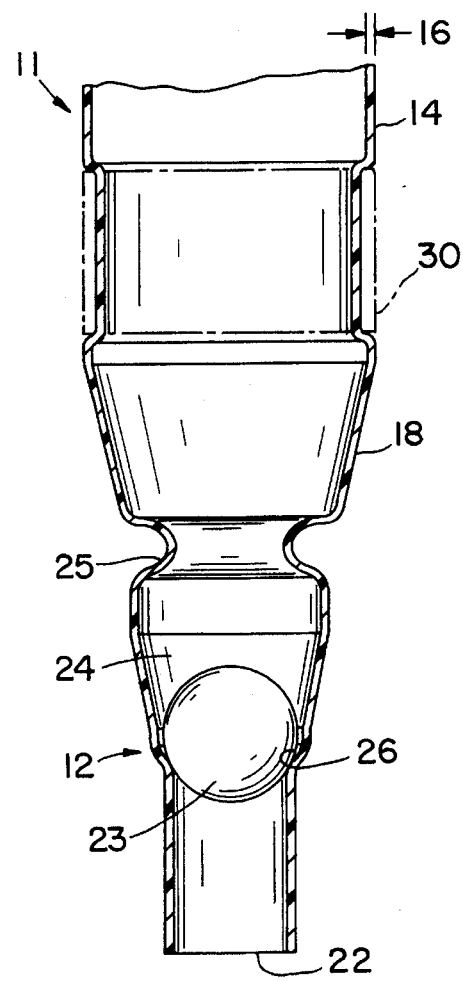
FIG. 2 is a view partly in section of an inlet valve means portion of the disposable bailer.

The preferred embodiment of the bailer 11 is shown in FIG. 1, with the preferred embodiment of the check valve being shown in both FIGS. 1 and 2. The bailer 11 is a tube with tapered upper and lower ends 17, 18. The bailer body contains ridges 15 to provide for increased stiffness. The upper end 17 being tapered and having a pour spout 21 and suspension cord holes 20. The lower inlet end 18 providing a cavity 24 for the ball 23 which functions as a check valve 12 by further including indentations or a depression 25 and a molded-in valve seat 26 on which the ball 23 rests.

It is further possible to add an outlet valve means consisting of a second ball which functions as a check valve on the top tapered end of the bailer. When the bailer has reached the predetermined depth, and ascent begun, both upper and lower check balls will seat, effectively isolating the sample taken at that depth within the bailer. The upper check valve seat can be molded into the top section of the bailer in a similar fashion to that described for the lower check valve. Indentations 25 would retain the ball, preventing its loss. The term bailer for purposes of this application means liquid sampling, device. Also to increase its weight and positive displacement into a body of liquid, the bailer may have a metal or other dense material ring 30 attached to the lower end thereof as shown in phantom lines in FIG. 2.

The bailer 11 can be produced by several forming techniques. These are for example extrusion blow molding, vacuum forming, roto molding, and electrostatic spraying.

In use, the bailer 11 is lowered by a suspension cord into a well or open body of water. As it descends, the ball which functions as a check valve at the bottom is forced up by reaction force from the liquid allowing the liquid being sampled to fill the bailer. As the filled bailer is withdrawn, the check valve closes, capturing the contents within the body of the bailer.

After the bailer is withdrawn completely from a well, a body of water or a container of liquid, its contents may then be emptied into appropriate sample collection containers either by decanting through the upper pour spout or by actuating the check valve at the bottom of the bailer.

The check valve can be actuated in a rather novel way by simply squeezing, with light finger pressure, the portion of the bailer bottom adjacent to the ball of the check valve. The squeezing action temporarily unseats the ball by changing the configuration of the flexible valve seat, thus causing the contents to be discharged. The dispensing flow rates can be closely controlled by varying the finger pressure. Controlling the flow rates is important to the user in that aeration and splashing of the sample can be minimized. Also, with the release of finger pressure, flow stops immediately, permitting the user to fill multiple vials without undue spillage. This is particularly important where the contents may be potentially toxic or hazardous in nature.

Rapid dispensing of the bailer's contents into larger containers may be accomplished by decanting or pouring from the pour spout located near the top of the bailer. This involves tilting the bailer slowly toward the horizontal until pouring occurs. Because of the special design of the check valve and bailer body, the premature dislodging or unseating of ball is prevented until the bailer is in a near horizontal position, i.e. essentially emptied. Thus the chance of unexpected spillage through the bottom inlet valve is reduced.

It is understood that various other modifications will be apparent to and can be readily made by those skilled in the art without departing from the scope and spirit of the present invention. Accordingly, it is not intended that the scope of the claims appended hereto be limited to the description set forth above but rather that the claims be construed as encompassing all of the features of patentable novelty which reside in the present invention, including all features which would be treated as equivalents thereof by those skilled in the art to which the invention pertains.

What is claimed is:

1. A disposable bailer comprising:

an one piece elongated tube constructed of a resilient polymeric material with lower fluid inlet and upper fluid outlet ends of the tube, both ends being integral with the tube and tapered;

an inlet valve comprising an upwardly facing conical valve seat formed in the tapered lower fluid inlet end of said tube and a valve member for engaging said valve seat from above, the tapered lower fluid inlet end of said tube being constricted to a dimension sufficiently narrow to constrain longitudinal motion of the valve member upwardly out of the tapered lower fluid inlet end of said tube;

the inlet end of the tube being continuously molded with the tube to form an internal cavity in the tapered portion of the inlet end for containing said valve member.

2. The disposable bailer in claim 1, wherein said valve member comprises a ball.

3. The disposable bailer in claim 1, wherein the elongated tube has at least one ridge for added stiffness.

4. The disposable bailer in claim 1, including an outlet means.

5. The disposable bailer in claim 4, wherein said outlet means includes at least one pour spout.

6. The disposable bailer in claim 1, including at least one hole in the upper fluid outlet end of said tube for facilitating suspension of said disposable bailer.

7. The disposable bailer in claim 1, including an outlet valve means.

* * * * *